US00PP28908P2

(12) United States Plant Patent
Korlipara

(10) Patent No.: US PP28,908 P2
(45) Date of Patent: Jan. 30, 2018

(54) ***SCROPHULARIA MACRANTHA* PLANT NAMED 'TNSCRCR'**

(50) Latin Name: *Scrophularia macrantha*
Varietal Denomination: TNSCRCR

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/330,804

(22) Filed: Nov. 7, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Annette H Para
(74) *Attorney, Agent, or Firm* — Klarquist Sparkman, LLP

(57) ABSTRACT

A new and distinct form of *Scrophularia macrantha* plant characterized by deep rose red flowers in dense paniculate cymes, blooms all summer, a short upright shrubby habit, excellent branching with flower spikes at end of every branch, and excellent vigor.

1 Drawing Sheet

Botanical denomination: *Scrophularia macrantha.*
Variety designation: 'TNSCRCR'.

BACKGROUND OF THE INVENTION

The present invention relates to a new and distinct cultivar of *Scrophularia macrantha*, given the name, 'TNSCRCR'. *Scrophularia* is in the family Scrophulariaceae. This new cultivar was part of a planned breeding program for a shorter *Scrophularia macrantha*. The parents were proprietary, unreleased seedlings of *Scrophularia macrantha. Scrophularia macrantha*, commonly known as Red Birds in a Tree or New Mexican Figwort, is a rare native of the mountains of New Mexico which blooms all summer with charming, small reddish flowers that resemble birds. It is also drought tolerant and loved by hummingbirds. Normal height for this plant is three to four feet.

Compared to the representative members of the species *Scrophularia macrantha*, the new cultivar is much shorter with denser inflorescences of deep rose red. Compared to the specific male and female *Scrophularia macrantha* parent seedlings, the new cultivar is shorter, better branched, and has larger flowers.

The new cultivar exhibits the following characteristics:

1. deep rose red flowers in dense paniculate cymes,
2. blooms all summer,
3. a short upright shrubby habit,
4. excellent branching with flower spikes at end of every branch, and
5. excellent vigor.

The new variety has been reproduced only by asexual propagation (stem cuttings and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows 7 month-old *Scrophularia macrantha* 'TNSCRCR' (with a with background) in July grown in a gallon container in full sun in Canby, Oreg.

FIG. 2 shows 7 month-old *Scrophularia macrantha* 'TNSCRCR' growing full sun in the trial field in July in Canby, Oreg.

DETAILED PLANT DESCRIPTION

The following is a detailed description of the new *Scrophularia macrantha* cultivar based on observations of 7 month-old specimens grown outside in the sun in the trial field in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, $5^{th}$ edition.

Plant:

*Form.*—Upright and bushy.
*Type.*—Evergreen, subshrub/perennial.
*Cold hardiness.*—USDA Zone 5-10.
*Size.*—Grows to 50 cm wide and 55 cm tall, including flowers.
*Vigor.*—Excellent.
*Branching.*—Extremely well-branched with about 5 main stems from the ground.
*Roots.*—Fibrous, freely branching, Greyed Orange 164D; plants root easily from stem cuttings.

Stem:

*Size.*—Grows to about 25 cm long and 4 mm wide.
*Internodes.*—4 cm to 5 cm long on main branches.
*Surface.*—Glandular pubescent.
*Color.*—Yellow Green 148B.

Leaf:

*Type*.—Simple, aromatic.

*Arrangement*.—Opposite.

*Blade size*.—Grow to 65 mm long and 38 mm wide.

*Shape*.—Deltoid to lanceolate.

*Venation*.—Pinnate, Yellow Green 146B on both sides.

*Margins*.—Coarsely serrate (sometimes biserrate) to dentate.

*Apex*.—Acute.

*Base*.—Truncate to cuneate.

*Surface texture*.—Both sides glabrous.

*Petiole description*.—6 mm to 25 mm long and 1 mm to 3 mm wide, glabrous, Yellow Green 146B.

*Leaf color*.—Top side Green N137D, bottom side closest to Yellow Green 147B.

Inflorescence:

*Type*.—Terminal paniculate cyme.

*Number of flowers*.—About 250 per cyme.

*Size of inflorescence*.—Grows to 24 cm long and 9 cm wide.

*Peduncle*.—Grows to 4.5 cm long from terminal leaves to base of inflorescence, Yellow Green 148B, glandular pubescent.

*Pedicel*.—3 mm long and 1 mm wide, glandular pubescent, Yellow Green 148B.

*Bloom period*.—Middle of May to October in Canby, Oreg.

Flower bud:

*Size*.—10 mm long and 5 mm wide at the widest point prior to opening.

*Description*.—Bulbous.

*Surface texture*.—Glandular pubescent.

*Color*.—Greyed Purple 185C.

Flower:

*Type*.—Perfect.

*Shape*.—Zygomorphic, tubular.

*Corolla description*.—7 mm wide and 19 mm long; glandular pubescent outside and glabrous inside, margins entire; tube 10 mm long and 7 mm wide; 4 main lobes in two lips, upper lip prominent, 5 mm wide and 5 mm long, with two overlapping lobes, ovate with tips obtuse; lower lip 3-lobed with two side lobes, 3 mm long and 4 mm wide, tip obtuse, bottom lobe slightly reflexed 2.5 mm long and 2 mm wide, tip obtuse; outside color between Red 46A and Red Purple 60A, inside closest to Greyed Red 181D.

*Calyx description*.—5-lobed, 5 mm wide and 4 mm deep, lobes ovate, 2 mm long and 2 mm wide, tips acute, margins entire, Yellow Green 147B on both sides, glandular pubescent outside and glabrous inside.

*Pistil description*.—1, 11 mm long, ovary conical, 3 mm long and 2 mm wide, Yellow Green 145C, style 8 mm long, Greyed Purple 186D, stigma White NN155A.

*Stamen description*.—4 and 1 staminode, White 155A, staminode attached dorsally, 12 mm long and 0.5 mm wide, filaments 10 mm long and 0.5 mm wide, anthers 1.5 mm long and 2 mm wide, White 155B, pollen White NN155A.

*Fragrance*.—None.

*Lastingness*.—A cyme blooms for about 4 weeks on the plant.

Fruit: A capsule, 10 mm long and 4 mm wide, Brown 200A, fertility good.

Seed: Oval, Brown N200A.

Pests and diseases: The new cultivar is typical to the genus. No known resistances to pests or diseases. No problems have been found in Canby, Oreg.

I claim:

1. A new and distinct form of *Scrophularia macrantha* plant substantially as shown and described.

* * * * *

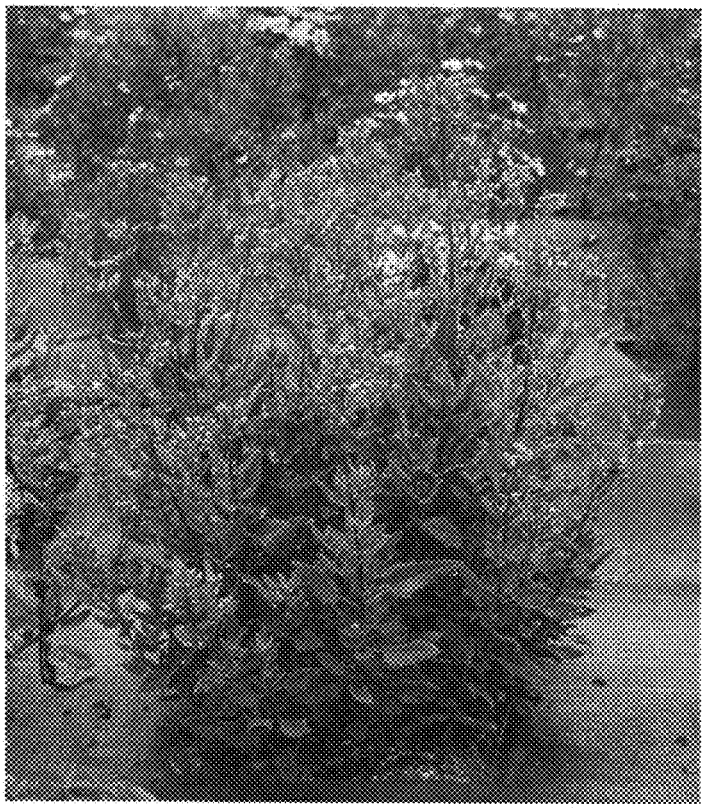

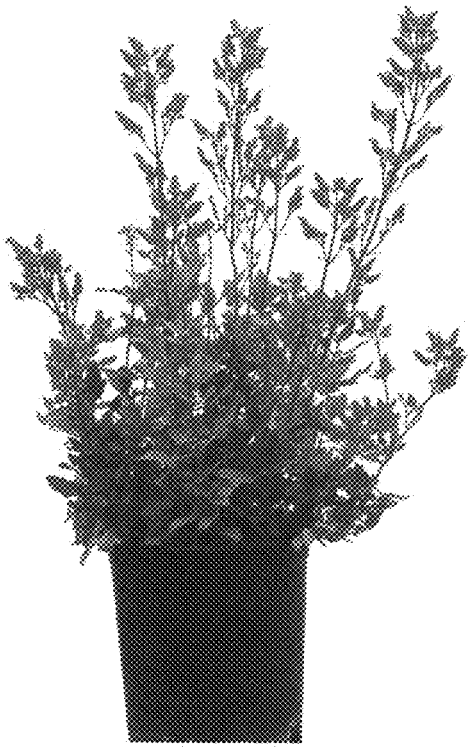
FIG. 1 on left
FIG. 2 below